(12) United States Patent
Zhang

(10) Patent No.: US 7,005,543 B2
(45) Date of Patent: Feb. 28, 2006

(54) METHOD OF PRODUCING BETAINE COMPOUND

(76) Inventor: Jiashu Zhang, 2704 S. George La., Diamond Bar, CA (US) 91765

( * ) Notice: Subject to any disclaimer, the term of this patent is extended or adjusted under 35 U.S.C. 154(b) by 0 days.

(21) Appl. No.: 10/888,741

(22) Filed: Jul. 9, 2004

(65) Prior Publication Data

US 2006/0009656 A1  Jan. 12, 2006

(51) Int. Cl.
*C07C 229/00* (2006.01)
(52) U.S. Cl. ..................................................... 562/575
(58) Field of Classification Search ................. 562/575
See application file for complete search history.

(56) References Cited

U.S. PATENT DOCUMENTS 5,696,287 A * 12/1997 Bellis .......................... 562/575

* cited by examiner

*Primary Examiner*—Paul A. Zucker
(74) *Attorney, Agent, or Firm*—Raymond Y. Chan; David & Ramond

(57) ABSTRACT

A process for preparing Anhydrous Betaine and Betaine Hydrochloride comprises treating a chloroacetic acid with sodium carbonate, and then dropping liquid trimethylamine to obtain Betaine products, wherein ion exchange resin and decompression process are utilized to assure the product having high purity and yield rate.

17 Claims, 2 Drawing Sheets

METHOD OF PRODUCING BETAINE COMPOUND

BACKGROUND OF THE PRESENT INVENTION

1. Field of Invention

The invention relates to a method for producing Betaine compound, and more particularly to an improved process for preparing Anhydrous Betaine and Betaine Hydrochloride in a high purity and high yield rate.

2. Description of Related Arts

Betaine, (also called Trimethylglycine or Oxyneurine), is naturally found in the metabolism of oxidation of choline. It, chemically 2-(Trimethylammonio) ethanoic acid, hydroxide, inner salt, donates a methyl group to homocysteine to produce Dimethylglycine and Methionine, which results a reduction in potentially toxic homocysteine levels. Synthesis of betaine in body tissue may not be high enough to meet the betaine needs of the animal, especially under stressful conditions. So it is an essential supplement in the feed industry. Commercially, synthetic betaine is available as anhydrous betaine (no water of crystallization), Betaine monohydrate (with water of hydration) and a stable salt form of Betaine monohydrochloride (with 25% hydrochloride to preserve betaine from degradation in storage and acts as an acidifier in applications).

Betaine anhydrous is one of betaine series. It is a kind of efficient, high-quality and economical nutritional additive promoting growth and widely used for animal, poultry and aquatic breeding.

Furthermore, as an efficient methyl supplier, it can partly take the place of methionine and choline chloride, and lower the cost of feed. Its effective value of organism is 3 times that of DL-methionine and 1.8 times that of 50% choline chloride. More importantly, it could promote the metabolism of fat, improve the lean meat rate of animal and poultry and the quality of meat, and lower the ratio of feed and meat. Meanwhile, it could lead to good appetite for animal and make the feed more agreeable to the taste of animal. In other words, it is an ideal pharmaceutical for promoting the growth of poultry and aquatic animal. Other beneficial factors of Anhydrous Betaine include maintaining the stability of vitamin in feed and the function of intestines.

Commonly, the conventional producing method to prepare Anhydrous Betaine and Betiane Hydrochloride includes treating a chloroacetic acid with sodium carbonate, and then dropping liquid trimethylamine to obtain Betaine products.

However, the quality and the purity of the conventional producing method are not satisfied. It is highly desirable to develop a producing method for preparing Anhydrous Betaine and Betaine Hydrochloride having higher yield rate and purity.

SUMMARY OF THE PRESENT INVENTION

A main object of the present invention is to provide a producing method for the preparation of a betaine compound, such as anhydrous betaine and betaine hydrochloride, in high yield rate and high purity.

Accordingly, to achieve the above object, the present invention provides a producing process for preparing Anhydrous Betaine and Betaine Hydrochloride respectively, comprising the steps of:

a. mixing sodium carbonate with chloroacetic acid to form a solution A;

b. dropping liquid trimethylamine into the solution A to form a solution B at a predetermined temperature and pH value;

c. decompressing the solution B until a betaine compound crystal is formed; and d. centrifugalizing and drying the betaine compound crystal to form the betaine compound.

These and other objectives, features, and advantages of the present invention will become apparent from the following detailed description, the accompanying drawings, and the appended claims.

DETAILED DESCRIPTION OF THE PREFERRED EMBODIMENT

Figure 1:
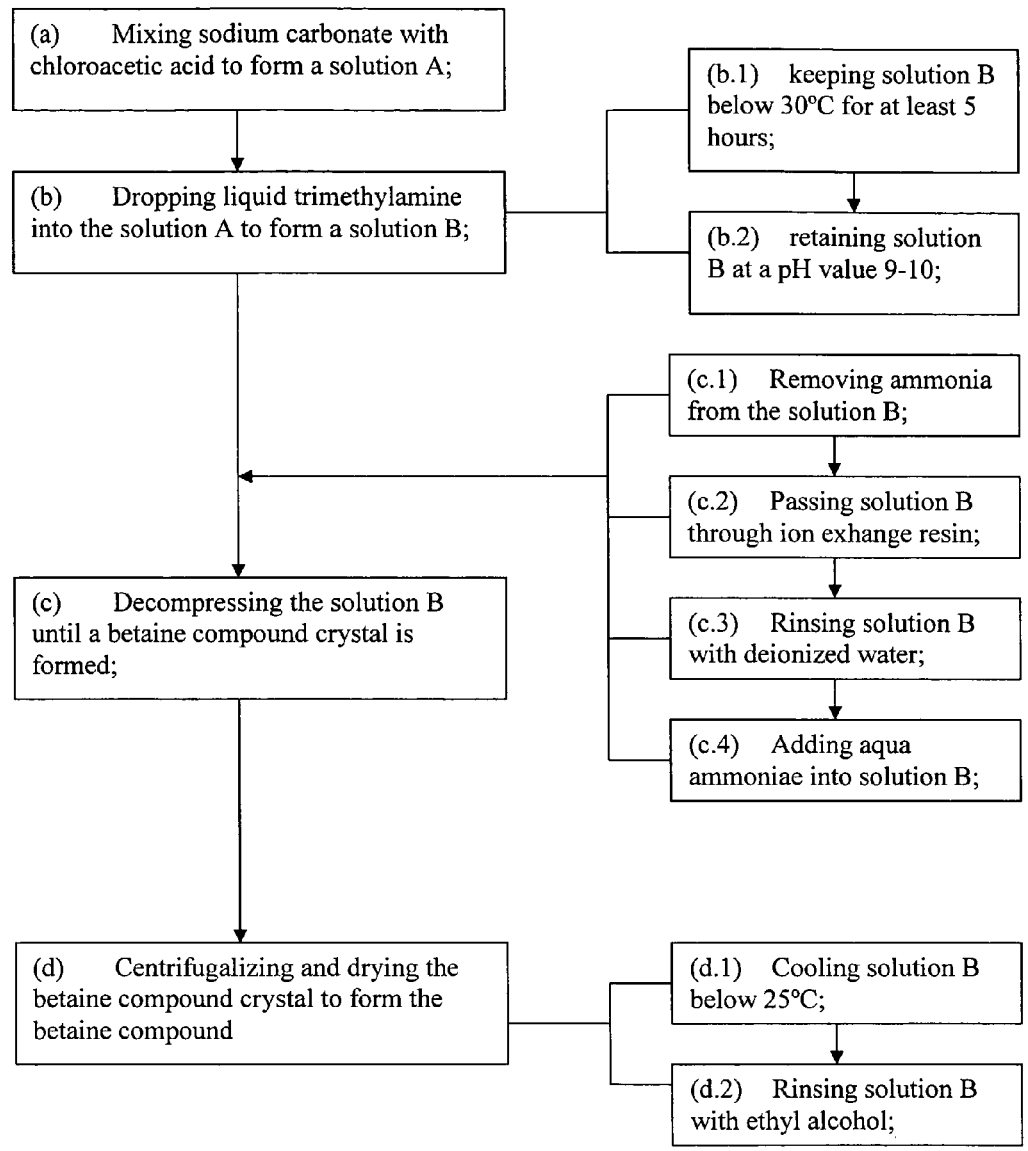
FIG. 1 is a block diagram showing the producing method for preparing Anhydrous Betaine according to the first preferred embodiment of the present invention.
Figure 2:
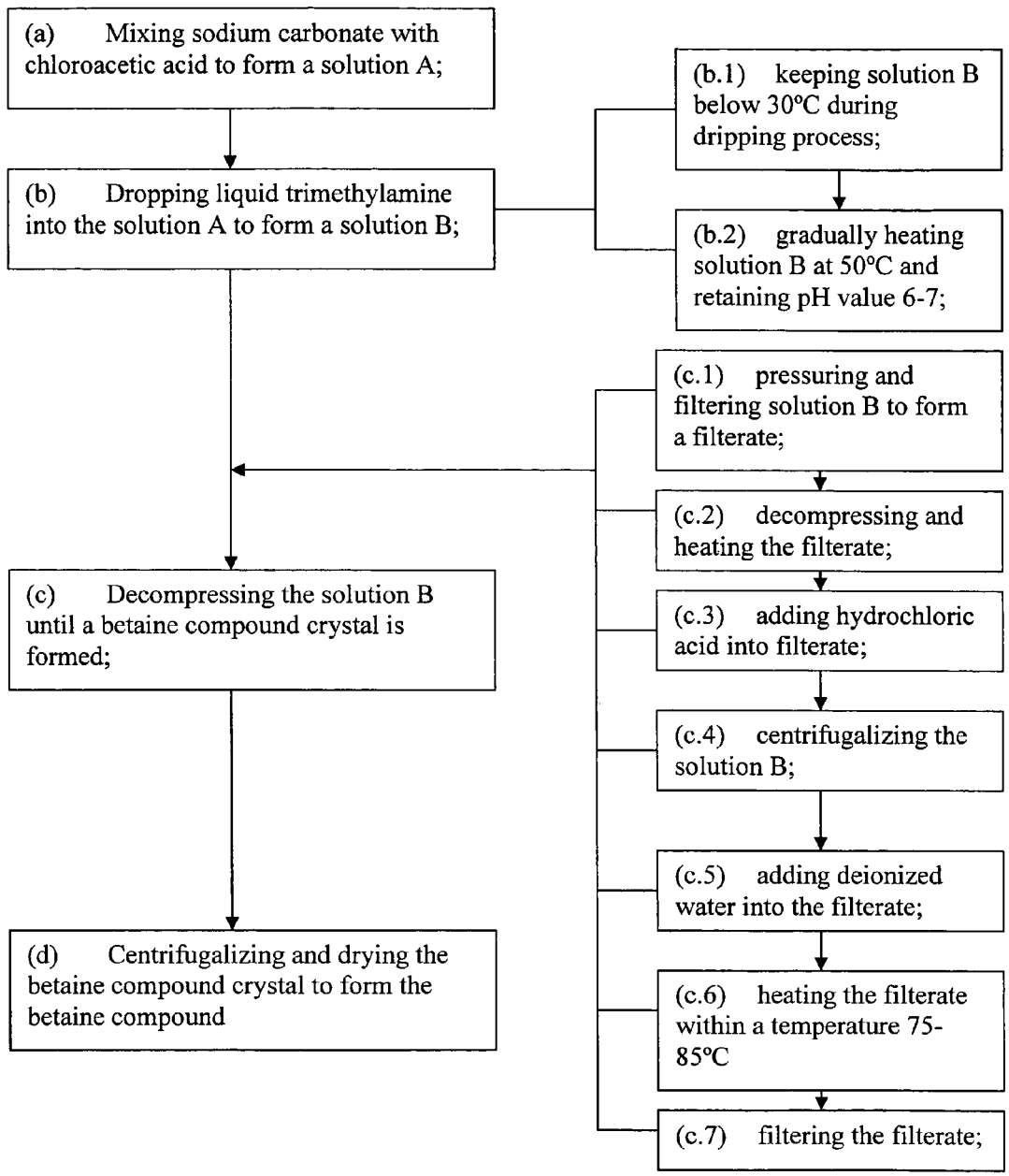
FIG. 2 is a block diagram showing the producing method for preparing Betaine Hydrochloride according to the second preferred embodiment of the present invention.

Referring to the FIG. 1 and FIG. 2, a producing method for preparing Bataine Compounds according to the first preferred embodiment of the present invention is illustrated. The producing method comprises the following steps:

a. mixing sodium carbonate with chloroacetic acid to form a solution A;

b. dropping liquid trimethylamine into the solution A to form a solution B at a predetermined temperature and pH value;

c. decompressing the solution B until a betaine compound crystal is formed; and d. centrifugalizing and drying the betaine compound crystal to form the betaine compound.

According to the first preferred embodiment, before the step (c), the process further comprises the steps of:

(c.1) removing ammonia from the solution B until the solution B has a pH value within a range between 7 and 8;

(c.2) passing the solution B through ion exchange resin;

(c.3) rinsing the solution B with deionized water until chlorine anion is removed from the solution B; and (c.4) adding aqua ammoniae into the solution B.

Embodiment 1

In this embodiment, the present invention provides a process for preparing anhydrous betaine. According to the present invention, in the step (a), 120 kg of chloroacetic acid are added to 180 kg of water with stirring until the chloroacetic acid is completely dissolved, and then 70 kg of sodium carbonate are slowly added into the diluted chloroacetic acid to form a solution A. At the same time, the pH value of solution A is adjusted at 6.5–7.5.

In the step (b), 283 liters liquid trimethylamine (30%) are dropped into the solution A at 25° C.–30° C. to form a solution B. Afterwards, the solution B is kept 5 hours at a temperature below 30° C. and with a pH value 9–10.

In the step (c.1), the solution B is decompressed to remove ammonia until the pH value at a range 7–8, and then 4000 liters of water are added into solution B for dilution purpose.

In the step (c.2), the diluted solution B is passed through an ion exchange resin and, in the step (c.3), the diluted solution B is rinsed by deionized water till chlorine anion is removed.

In the step (c.4), aqua ammoniae (2.5%) is added to the diluted solution B.

In the step c, the solution B is collected (1500–1800 liters), decompressed and concentrated till some crystals appearing.

In the step (d), the crystallized solution B is cooled down below 25° C. Afterwards, it is centrifugalized and rinsed with ethyl alcohol, then dried, obtaining anhydrous betaine.

In view of the fine product of Anhydrous Betaine, the appearance is white powder or granule. Furthermore, a series of property test is subsequently followed to test the final product of Anhydrous Betaine.

TABLE 1

Property of the Anhydrous Betaine made by the producing method according to the first preferred embodiment of the present invention

| | |
|---|---|
| MOLECULAR FORMULA | C5H11NO2 |
| MOLECULAR WEIGHT | 117.15 |
| APPEARANCE | White powder or granule |
| WATER CONTENT | <2% |
| RESIDUE ON IGNITION | <0.1% |
| ANHYDROUS BETAINE | 98.5% |

As shown in above table 1, the Anhydrous Betaine prepared by the producing method according to the first preferred embodiment of the present invention has a distinguished property with water content less than 2%, residue on ignition less than 0.1%, and Anhydrous Betaine content more than 98.5%.

Embodiment 2

Referring to the FIG. 2, the producing method of Betaine Hydrochloride according to the second preferred embodiment of the present invention is illustrated. The producing method for preparing Betaine Hydrochloride comprises the following steps:

e. mixing sodium carbonate with chloroacetic acid to form a solution A;

f. dropping liquid trimethylamine into the solution A to form a solution B at a predetermined temperature and pH value;

g. decompressing the solution B until a betaine compound crystal is formed; and h. centrifugalizing and drying the betaine compound crystal to form the betaine compound.

According to the second preferred embodiment, before the step (c), the process further comprises the steps of:

(c.1) pressuring and filtering the solution B for concentration, until a filtrate thereof becomes clear;

(c.2) decompressing and heating the filtrate of the solution B for water evaporating;

(c.3) adding hydrochloric acid into the filtrate of the solution B;

(c.4) centrifugalizing the solution B;

(c.5) adding deionized water into the filtrate;

(c.6) heating the filtrate at a temperature within a range between 75–85° C.; and (c.7) filtering the filtrate.

According the second preferred embodiment of the present invention, in the step (a), 200 kg of chloroacetic acid are added to 200 kg of water with stirring, until chloroacetic acid is dissolved completely. Afterwards, 100 kg of sodium carbonate are added to the diluted chloroacetic acid slowly at 40° C. and pH 4.5–5.5 to form solution A. Then, the pH value of the solution A is adjusted to 7.0–7.5.

In the step (b), 550 kg trimethylamine (30%) are dropped into the solution A at a temperature below 20° C. to form solution B, and the temperature is controlled at a temperature below 30° C. during the dropping process. Afterwards, the solution B is heated with stirring, controlling rising 5° C. per half hour. Stop heating at 50 degree C. Then, the pH value of solution B is adjusted at 6–7.

In the step (c.1), the solution B is pressured and filtered for concentration to form a filterate. In the step (c.2), after the filterate is checked clear, the filterate is decompressed and heated for water evaporating. Afterwards, check the density of solution B at 1.2–1.3. The heating process is stopped and the solution B is cooled down at a temperature less than 35° C.

In the step (c.3), 220 liters of hydrochloric acid are added to the filterate of solution B, stirring until the temperature below 25° C. And then in the step (c.4), the solution B is centrifugalized to obtain a semifinished product of betaine hydrochloride.

In the step (c.5), the semifinished product obtained from step (c.4) is added to deionized water which is 2–2.5 times of weight of the semifinished product. In the step (c.6) the semifinished product is stirred and heated until the temperature at 75–85° C. In the step (c.7), the semifinished product is filterated.

In the step c, the filterated semifinished product is decompressed until some crystals appearing, then cooling down the temperature below 25° C.

In the step (d), the crystallized semifinshed product is centrifuglized and dried, obtaining fine product of betaine hydrochloride, and parent solution is used for next super fine process.

In view of the fine product of Betaine Hydrochloride, the appearance is white crystal granule. Furthermore, a series of property test is subsequently followed to test the final product of Betaine Hydrochloride.

TABLE 2 property of the Betaine Hydrochloride made by the producing method according to the first preferred embodiment of the present invention

| | |
|---|---|
| MOLECULAR FORMULA | C5H11NO2HCL |
| MOLECULA WEIGHT | 153.61 |
| APPEARANCE | White crystal granule |
| WATER CONTENT | <0.5% |
| ACIDITY | pH = 0.8–1.2 |
| RESIDUE ON IGNITION | <0.1% |
| ARSENIC | <2 ppm |
| HEAVY METALS | <10 ppm |
| BETAINE HYDROCHLORIDE CONTENT | 98.0–100.5% |

As shown in the table 2, the Betaine Hydrochloride Anhydrous Betaine prepared by the producing method according to the second preferred embodiment of the present invention has a distinguished property with water content less than 0.5%, residue on ignition less than 0.1%, arsenic less than 2 ppm, heavy metals less than 10 ppm, and Betaine Hydrochloride content within a range between 98.0 to 100.5%.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles

What is claimed is:

1. A process for preparing a betaine compound, comprising the steps of:
   (a) mixing sodium carbonate with chloroacetic acid to form a solution A;
   (b) dropping liquid trimethylamine into said solution A to form a solution B at a predetermined temperature and pH value;
   (c) decompressing said solution B until a betaine compound crystal is formed; and
   (d) centrifugalizing and drying said betaine compound crystal to form said betaine compound.

2. The process as recited in claim 1, before the step (c), further comprising the steps of:
   (c.1) removing ammonia contained in said solution B from said solution B until said solution B has a pH value within a range between 7 and 8 and adding a predetermined amount of water into said solution B to form a diluted solution B;
   (c.2) passing said diluted solution B through ion exchange resin;
   (c.3) adding deionized water into said diluted solution B to rinse said diluted solution B until chlorine anion contained in said diluted solution B is removed from said diluted solution B; and
   (c.4) adding aqua ammoniae into said diluted solution B.

3. The process, as recited in claim 2, wherein said betaine compound is anhydrous betaine.

4. The process as recited in claim 2, in step (a), wherein a ratio of said sodium carbonate and said chloroacetic acid is 7:12 by weight to form said solution A having a pH value within a range between 6.5 and 7.5.

5. The process as recited in claim 3, in step (a), wherein a ratio of said sodium carbonate and said chloroacetic acid is 7:12 by weight to form said solution A having a pH value within a range between 6.5 and 7.5.

6. The process as recited in claim 3, in step (b), further comprising the steps of:
   (b.1) keeping said solution B below 30° C. for at least 5 hours; and
   (b.2) retaining said solution B at a pH value within a range between 9 and 10.

7. The process as recited in claim 5, in step (b), further comprising the steps of:
   (b.1) keeping said solution B below 30° C. for at least 5 hours; and
   (b.2) retaining said solution B at a pH value within a range between 9 and 10.

8. The process as recited in claim 3, further comprising the steps of:
   (d.1) cooling said solution B below 25° C.; and
   (d.2) adding ethyl alcohol into said solution B to rinse said solution B before said solution B is dried.

9. The process as recited in claim 5, further comprising the steps of:
   (d.1) cooling said solution B below 25° C.; and
   (d.2) adding ethyl alcohol into said solution B to rinse said solution B before said solution B is dried.

10. The process as recited in claim 7, further comprising the steps of:
    (d.1) cooling said solution B below 25° C.; and
    (d.2) adding ethyl alcohol into said solution B to rinse said solution B before said solution B is dried.

11. The process as recited in claim 1, before the step (c), further comprising the steps of:
    (c.1) pressuring and filtering said solution B for concentration, until a filtrate thereof becomes clear;
    (c.2) decompressing and heating said filtrate of said solution B for water evaporating;
    (c.3) adding hydrochloric acid into said filtrate of said solution B;
    (c.4) centrifugalizing said solution B;
    (c.5) adding deionized water into said filtrate;
    (c.6) heating said filtrate at a temperature within a range between 75–85° C.; and
    (c.7) filtering said filtrate.

12. The process, as recited in claim 11, wherein said betaine compound is betaine hydrochloride.

13. The process as recited in claim 11, in step (a), wherein a ratio of said sodium carbonate and said chloroacetic acid is 1:2 by weight to form said solution A having a pH value within a range between 7.0 and 7.5.

14. The process as recited in claim 12, in step (a), wherein a ratio of said sodium carbonate and said chloroacetic acid is 1:2 by weight to form said solution A having a pH value within a range between 7.0 and 7.5.

15. The process as recited in claim 11, in step (b), further comprising the steps of:
    (b.1) keeping said solution B below 30° C. when said liquid trimethylamine is dropped into said solution A; and
    (b.2) gradually heating said solution B at 50° C. and retaining said solution B at a pH value within a range between 6 and 7.

16. The process as recited in claim 12, in step (b), further comprising the steps of:
    (b.1) keeping said solution B below 30° C. when said liquid trimethylamine is dropped into said solution A; and
    (b.2) gradually heating said solution B at 50° C. and retaining said solution B at a pH value within a range between 6 and 7.

17. The process as recited in claim 14, in step (b), further comprising the steps of:
    (b.1) keeping said solution B below 30° C. when said liquid trimethylamine is dropped into said solution A; and
    (b.2) gradually heating said solution B at 50° C. and retaining said solution B at a pH value within a range between 6 and 7.

* * * * *